United States Patent [19]

Masada et al.

[11] Patent Number: 5,011,824

[45] Date of Patent: Apr. 30, 1991

[54] RECTAL MOTILIN PREPARATION

[75] Inventors: Tomoaki Masada; Yasuhiko Ueno; Eiji Hayakawa; Hirotake Naganuma; Mitsuru Terajima; Tokuyuki Kuroda; Katsuichi Shuto; Shunji Ichikawa, all of Shizuoka, Japan

[73] Assignee: Kyowa Hakko Kogyo Co., Ltd., Tokyo, Japan

[21] Appl. No.: 436,058

[22] Filed: Nov. 13, 1989

[30] Foreign Application Priority Data

Nov. 16, 1988 [JP] Japan .................... 63-289564
Jul. 3, 1989 [JP] Japan .................... 64-171604

[51] Int. Cl.$^5$ ................... A61K 37/24; A61K 37/36
[52] U.S. Cl. ................................... 514/13; 514/12
[58] Field of Search .......................... 514/13, 12

[56] References Cited

U.S. PATENT DOCUMENTS 4,434,159 2/1984 Sekine et al. ................ 514/12 X
4,464,363 8/1984 Higuchi et al. ............... 514/13 X

FOREIGN PATENT DOCUMENTS 1507248 4/1978 United Kingdom .

OTHER PUBLICATIONS

Regul. Peptides 15 (1986), 333–339, Peeters et al.
Regul. Peptides 23 (1988), 171–182, Peeters et al.
Biomedical Research 9(5), 361–366 (1988), Peeters et al.

Primary Examiner—Howard E. Schain
Attorney, Agent, or Firm—Nixon & Vanderhye

[57] ABSTRACT

A motilin preparation in the form of a rectal suppository containing motilin together with a pH controller capable of adjusting the pH value of the intrarectal fluid to 8.0 to 10.0, which is highly useful as a rectal suppository.

16 Claims, 4 Drawing Sheets

RECTAL MOTILIN PREPARATION

FIELD OF THE INVENTION

This invention relates to a motilin preparation for rectal administration.

BACKGROUND OF THE INVENTION

Motilin is a gastrointestinal hormone which stimulates gastric motor activity in hunger. Motilin is considered to be useful as a therapeutic for, e.g., improving gastric motor activity.

Similar to common physiologically active peptides, motilin is hardly absorbed orally since it shows poor gastrointestinal absorptivity. Such physiologically active substances showing poor oral absorption are generally administered through injection. However, injection is not a preferred route of administration because it is painful, there are potential risky side effects including amyotrophy, it is inconvenient, particularly for individual patient use, and is often limited to institutional treatments.

Recently rectal administration of drugs has again been considered and the administration of, in particular, physiologically active peptides in the form of suppositories has attracted attention. However, there is no motilin preparation suitable for rectal administration capable of maintaining a therapeutically effective blood concentration of motilin, since it is only slightly absorbed if at all through the rectum.

Accordingly, motilin preparations for rectal administration, whereby the absorption of motilin through the rectum is promoted, are needed.

SUMMARY OF THE INVENTION

We have conducted extensive studies on motilin preparations for rectal administration in which the rectal absorption of motilin is promoted. As a result, we have found that the rectal absorption of motilin can be promoted by adding a pH controller capable of adjusting the pH value of the intrarectal fluid to 8.0 to 10.0, a membrane-permeation promoter or a protease inhibitor, thus completing the present invention.

The present invention relates to a pharmaceutical composition for rectal administration containing a therapeutically effective quantity of motilin together with a pH controller capable of adjusting the pH value of the patient's intrarectal fluid to 8.0 to 10.0, which may further contain a membrane-permeation promoter and/or a protease inhibitor.

DETAILED DESCRIPTION OF THE INVENTION

Figure 1:
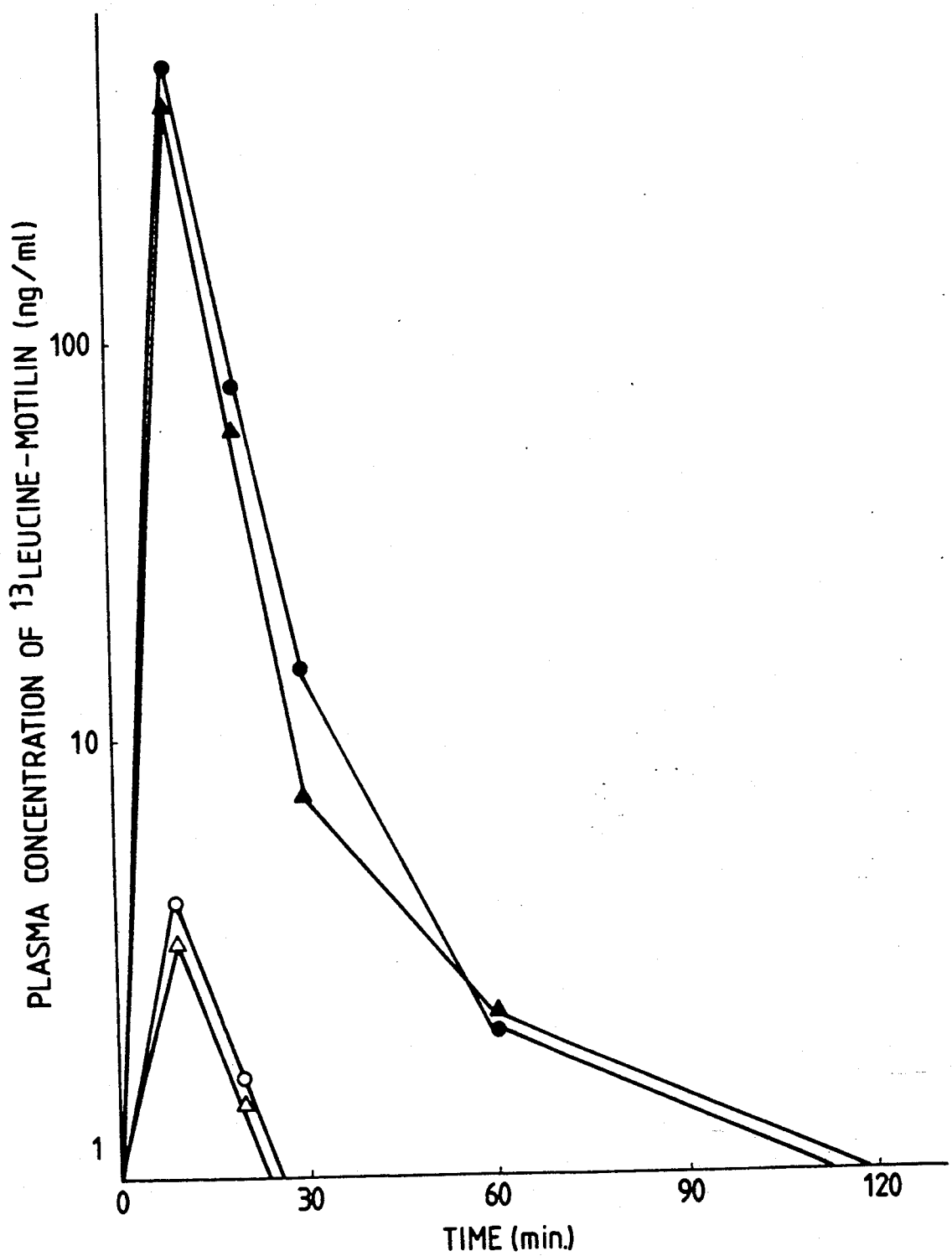
FIG. 1 shows the change in plasma concentration of $^{13}$leucine-motilin as the result of Test Example 2, wherein -●- shows the suppository of Example 1, -▲- shows that of Example 2, -○- shows that of Reference Example 1 and -△- shows that of Reference Example 2.

The motilin to be used in the present invention may be from various sources such as extracted from an animal organ, chemically synthesized or prepared by DNA recombination techniques. Examples thereof include swine motilin [cf. Can. J. Physiol. Pharmacol., 49, 399–405 (1971)], canine motilin [cf. Regul. Peptides, 5, 197–208 (1983)] and $^{13}$leucine-swine motilin wherein the methionine at the 13-position of swine motilin is substituted with
leucine [cf. U.S. Ser. No. 094,886 filed on Sept. 10, 1987 or JP-A-63-71195 (the term "JP-A" as used herein means "an unexamined published Japanese patent application)]. Human motilin has the same structure as that of swine motilin [cf. Federation of European Biochemical Societies, 233 (1), 74–76 (1987)].

The motilin may be either in a free state or in the form of an organic or inorganic acid salt. It is desirably homogeneously dispersed or dissolved in the preparation.

The preparation usually contains a therapeutically effective quantity, suitably about 0.05 to about 5% by weight, preferably about 0.1 to about 2% by weight, of motilin. Motilin is reasonably safe so that when 10 mg/kg of the same motilin as contained in the preparation was intravenously administered to rats, animal did not die.

The pH controller to be used in the present invention may be selected from those commonly used in drugs and capable of adjusting the pH value of the intrarectal fluid to 8.0 to 10.0, preferably 8.5 to 9.5, after the administration of the preparation. The normal pH value of the intrarectal fluid usually ranges from 7.0 to 8.0. Since motilin and conventionally employed bases are weakly acidic, it is difficult to maintain the pH value of the intrarectal fluid within a range of 8.0 to 10.0 without the use of a pH adjusting/increasing agent.

Examples of suitable pH controllers include combinations of hydrochloric acid/sodium barbital, hydrochloric acid/trisaminomethane, hydrochloric acid/sodium borate, hydrochloric acid/aminomethylpropanediol, hydrochloric acid/sodium dimethylglycinate, sodium carbonate/sodium bicarbonate, sodium carbonate/sodium borate, monobasic potassium phosphate/sodium borate, ammonium chloride/ammonia, glycine/sodium hydroxide and glycine/arginine. Preferable pH controllers are glycine/arginine and sodium carbonate/sodium bicarbonate. The mechanism for promoting the abrsorption of motilin by these pH controllers is not presently known.

In the present invention, any pharmaceutically acceptable membrane-permeation promoter may be used. Bile acids and fatty acids having 6 to 18 carbon atoms are preferred. Examples of the bile acids include glycolic, taurocholic, deoxycholic, glycodeoxycholic, taurodeoxycholic and ursodeoxycholic acids and salts thereof, fusidic acid and salts thereof, fusidic acid derivatives and salts thereof, and glycyrrhizin and derivatives thereof. The fatty acids typically contain 6 to 18 carbon atoms and may be either straight-chained or branched. Examples thereof include caproic, capric, caprylic, lauric, palmitic, palmitoleic, stearic, oleic, linolenic and linoleic acids and salts thereof. It is particularly preferably to use straight-chain saturated fatty acids having 8 to 12 carbon atoms such as caprylic, capric and lauric acids and salts thereof.

Any protease inhibitor may be used in the present invention so long as it is pharmaceutically acceptable. Examples include peptide protease inhibitors such as aprotinin, bacitracin, colistin and polymyxin B and compounds having a sulfhydryl group such as cysteine. Among these, L-cysteine and colistin are preferably used.

Generally speaking, proteases such as aminopeptidase, carboxypeptidase and collagenase are present in various mucosa tissues such as rectal mucosa. These enzymes would decompose administered peptides. The above-mentioned protease inhibitors inhibit the activities of these enzymes to prevent the decomposition of peptides. Presence of a protease inhibitor increases the amount of the peptide, in this case motilin, therapeutically available to the patient.

These ingredients, the pH controller, membrane-permeation promoter and protease inhibitor, together with the usual pharmaceutical carriers, bases, diluents, adjuvants, coloring agents, perfumes or the like, are mixed with and desirably homogeneously dispersed or dissolved in the preparation.

The quantity of the pH controller, membrane-permeation promoter and protease inhibitor in the preparation are not particularly restricted and will easily be ascertained by the clinician and/or formulator. It is generally preferable that the pH controller and membrane-permeation promoter are both present in an amount of 0.1 to 20% by weight based on the weight of the preparation while the protease inhibitor is present in an amount of 0.01 to 25% by weight based on the preparation. More preferably, the pH controller, the membrane-permeation promoter and the protease inhibitor are used in an amount of 3 to 15% by weight, 2 to 10% by weight and 0.1 to 12% by weight, respectively, based on the weight of the preparation.

Either an oily ointment base or a water soluble cream base conventionally used in the art may be used in the preparation of the present invention. Examples of the oily base include vegetable fats and oils such as cacao fat, peanut oil, coconut oil and corn oil, hard fats comprising glycerol saturated fatty acid esters originating from natural fatty acids such a Witepsol ® (mfd. by Dynamit Nobel Co.) and Pharmasol ® (mfd. Nippon Oils & Fats Co., Ltd.) and mineral oils such as vaseline and paraffin.

Examples of the water soluble bases include polyethylene glycol/polypropylene glycol copolymer, propylene glycol and glycerol. These bases may be used alone or in combination.

The preparation of the present invention may be formulated into, for example, rectal suppositories or inserts which are in the form of a solid at room temperature or soft capsules in which a solution or an ointment is enclosed. The products may be formulated into insertable liquids for use as retention enemas.

The preparation of the present invention may additionally contain various additives commonly in the art, for example, surfactants such as sodium lauryl sulfate and polyoxyethylene lauryl ether, antioxidants such as butylhydroxytoluene, preservatives such as paraoxybenzoates and absorption promoters such as salicylic, caprylic and cholic acids, colorants, perfumes and the like.

The preparation of the invention can be administered at a dose of 1 to 100 mg for an adult 1 to 3 times per day. The dosage may vary depending on the age, body weight, conditions of the patient.

The following Examples, Reference Examples and Test Examples further illustrate the invention, but are not construed to limit the scope of the invention.

EXAMPLE 1

171.5 mg of Pharmasol ® B112 (mfd. by Nippon Oils & Fats Co., Ltd.) was melted at 45° C. Then 2.5 mg of $^{13}$leucine-swine motilin acetate, 23.0 mg of sodium bicarbonate and 3.0 mg of sodium carbonate were homogeneously dispersed therein. Next, the resulting mixture was charged into a plastic suppository mold and slowly cooled to thereby give a rectal suppository.

EXAMPLE 2

172.6 mg of Pharmasol ® B112 was melted at 45° C. Then 2.5 mg of $^{13}$leucine-swine motilin acetate, 14.4 mg of glycine and 10.5 mg of arginine were homogeneously dispersed therein. Next, the resulting mixture was charged into a plastic suppository mold and slowly cooled to thereby give a rectal suppository.

EXAMPLE 3

645.6 mg of Witepsol ® H15 (mfd. by Dynamit Nobel Co.) and 277.1 mg of Witepsol ® E75 (mfd. by Dynamit Nobel Co.) were melted at 40 to 50° C. Then 2.5 mg of $^{13}$leucineswine motilin acetate, 25.0 mg of sodium caprylate, 28.8 mg of glycine and 21.0 mg of arginine were homogeneously dispersed therein. Next, the resulting mixture was charged into a plastic suppository mold and slowly cooled to thereby give a rectal suppository.

EXAMPLE 4

645.6 mg of Witepsol ® H15 and 277.1 mg of Witepsol ® E75 were melted at 40 to 50° C. Then 2.5 mg of $^{13}$leuCine-swine motilin acetate, 25.0 mg of sodium deoxycholate, 28.8 mg of glycine and 21.0 mg of arginine were homogeneously dispersed therein. Next, the resulting mixture was charged into a plastic suppository mold and slowly cooled to thereby give a rectal suppository.

EXAMPLE 5

661.6 mg of Witepsol ® H15 and 283.6 mg of Witepsol ® E75 were melted at 40 to 50° C. Then 2.5 mg of $^{13}$leucine-swine motilin acetate, 2.5 mg of Colistin, 28.8 mg of glycine and 21.0 mg of arginine were homogeneously dispersed therein. Next, the resulting mixture was charged into a plastic suppository mold and slowly cooled to thereby give a rectal suppository.

EXAMPLE 6

617.7 mg of Witepsol ® H15 and 264.8 mg of Witepsol ® E75 were melted at 40 to 50° C. Then 2.5 mg of $^{13}$leuCine swine motilin acetate, 28.0 mg of cysteine hydrochloride and 87.0 mg of arginine were homogeneously dispersed therein. Next, the resulting mixture was charged into a plastic suppository mold and slowly cooled to thereby give a rectal suppository.

EXAMPLE 7

489.3 mg of Witepsol ® H15 and 209.7 mg of Witepsol ® E75 were melted at 40 to 50° C. Then 12.0 mg of $^{13}$leucine-swine motilin acetate, 90.0 mg of sodium decanoate, 115.0 mg of glycine and 84.0 mg of arginine were homogeneously dispersed therein. Next, the resulting mixture was charged into a plastic suppository mold and slowly cooled to thereby give a rectal suppository.

EXAMPLE 8

489.3 mg of Witepsol ® H15 and 209.7 mg of Witepsol E75 were melted at 40 to 50° C. Then 12.0 mg of $^{13}$leucine-swine motilin: acetate, 90.0 mg of sodium deoxycholate, 115.0 mg of glycine and 84.0 mg of arginine were homogeneously dispersed therein. Next, the resulting mixture was charged into a plastic suppository mold and slowly cooled to thereby give a rectal suppository.

EXAMPLE 9

489.3 mg of Witepsol ® H15 and 209.7 mg of Witepsol ® E75 were melted at 40 to 50° C. Then, 12.0 mg of $^{13}$leucine-swine motilin acetate, 12.0 mg of colistin, 78.0 mg of sodium chloride, 115.0 mg of glycine and 84.0 mg of arginine were homogeneously dispersed therein. Next, the resulting mixture was charged into a plastic suppository mold and slowly cooled to thereby give a rectal suppository.

EXAMPLE 10

367.5 mg of Witepsol ® H15 and 157.5 mg of Witepsol E75 were melted at 40 to 50° C. Then 12.0 mg of $^{13}$leucine-Swine motilin acetate, 115.0 mg of cysteine hydrochloride and 348.0 mg of arginine were homogeneously dispersed therein. Next, the resulting mixture was charged into a plastic suppository mold and slowly cooled to thereby give a rectal suppository.

EXAMPLE 11

645.6 mg of Witepsol H15 and 277.1 mg of Witepsol* E75 were melted at 40 to 50° C. Then 2.5 mg of $^{13}$methionine-swine motilin acetate, 25.0 mg of sodium decanoate, 28.8 mg of glycine and 21.0 mg of arginine were homogeneously dispersed therein. Next, the resulting mixture was charged into a plastic suppository mold and slowly cooled to thereby give a rectal suppository.

EXAMPLE 12

645.6 mg of Witepsol ® H15 and 277.1 mg of Wyiepsol ® E75 were melted at 40 to 50° C. Then 2.5 mg of $^{13}$methionine-swine motilin acetate, 25.0 mg of sodium deoxycholate, 28.8 mg of glycine and 21.0 mg of arginine were homogeneously dispersed therein. Next, the resulting mixture was charged into a plastic suppository mold and slowly cooled to thereby give a rectal suppository.

EXAMPLE 13

617.7 mg of Witepsol ® H15 and 264.8 mg of Witepsol ® E75 were melted at 40 to 50° C. Then 2.5 mg of $^{13}$methiOnine-swine motilin acetate, 28.0 mg of cysteine hydrochloride and 87.0 mg of arginine were homogeneously dispersed therein. Next, the resulting mixture was charged into a plastic suppository mold and slowly cooled to thereby give a rectal suppository.

EXAMPLE 14

663.4 mg of Witepsol H15 and 284.3 mg of Witepsol ® E75 were melted at 40 to 50° C. Then 2.5 mg of $^{13}$leucine-Swine mOtilin acetate, 28.8 mg of glycine and 21.0 mg of arginine were homogeneously dispersed therein. Next, the resulting mixture was charged into a plastic suppository mold and slowly cooled to thereby give a rectal suppository.

EXAMPLE 15

552.3 mg of Witepsol ® H15 and 236.7 mg of Witepsol ® E75 were melted at 40 to 50° C. Then 12.0 mg of $^{13}$leuCine-swine motilin acetate, 115.0 mg of glycine and 84.0 mg of arginine were homogeneously dispersed therein. Next, the resulting mixture was charged into a plastic suppository mold and slowly cooled to thereby give a rectal suppository.

EXAMPLE 16

663.4 mg of Witepsol ®H15 and 284.3 mg of Witepsol ® E75 were melted at 40 to 50° C. Then 2.5 mg of $^{13}$methionine-swine motilin acetate, 28.8 mg of glycine and 21.0 mg of arginine were homogeneously dispersed therein. Next, the resulting mixture was charged into a plastic suppository mold and slowly cooled to thereby give a rectal suppository.

REFERENCE EXAMPLE 1

197.5 mg of Pharmasol ® B112 was melted at 45° C. Then 2.5 mg of $^{13}$leucine-swine motilin acetate was homogeneously dispersed therein. The resulting mixture was charged into a plastic suppository mold and slowly cooled to thereby give a rectal suppository.

REFERENCE EXAMPLE 2

174.9 mg of Pharmasol ® B112 was melted at 45° C. Then 2.5 mg of $^{13}$leuCine-swine motilin acetate, 5.9 mg of monobasic potassium phosphate and 16.7 mg of dibasic sodium phosphate dihydrate were homogeneously dispersed therein. The resulting mixture was charged into a plastic suppository mold and slowly cooled to thereby give a rectal suppository.

TEST EXAMPLE 1

The motilin preparations obtained in Examples 1 and 2 and Reference Examples 1 and 2 were each thoroughly melted in 5 ml of a physiological saline solution heated to 40° C. The pH value of the resulting melted dispersion was measured with a pH meter.

TABLE 1

| Suppository | pH |
|---|---|
| Ex. 1 | 9.1 |
| Ex. 2 | 9.0 |
| R. Ex. 1 | 6.5 |
| R. Ex. 2 | 7.1 |

TEST EXAMPLE 2

The motilin suppositories prepared in Examples 1 and 2 and Reference Examples 1 and 2 were rectally administered to rabbits weighing approximately 2.5 kg (each group had six animals), which had fasted for 16 hours, each in a dose of 1.0 mg/kg. The blood of each animal was collected from its oticus vein 10, 20, 30, 60 and 120 minutes after the administration. Then the plasma was separated and the motilin concentration was determined by RIA. FIG. 1 shows the results, while Table 2 shows the time required for achieving the maximum blood concentration (Tmax), the maximum blood concentration (Cmax) and the area under the blood concentration-time curve ($AUC_3^\infty$).

TABLE

| Suppository | Tmax (min) | Cmax (ng/ml) | $AUC_0^\infty$ (ng · hr/ml) |
|---|---|---|---|
| Ex. 1 | 10 | 482.8 | 102.9 |
| Ex. 2 | 10 | 392.0 | 82.4 |
| R. Ex. 1 | 10 | 3.9 | 1.6 |
| R. Ex. 2 | 10 | 3.1 | 1.3 |

TEST EXAMPLE 3

The motilin suppositories prepared in Examples 3 to 6 and Reference Example 3 were rectally administered to rabbits each weighing approximately 2.5 kg (each group had six animals), which had fasted for 16 hours, each in a dose of 1.0 mg/kg.

The blood of each animal was collected from its oticus vein 5, 10, 20, 30, 60 and 120 minutes after the administration. Then the plasma was separated and the motilin concentration was determined by RIA.

Figure 2:
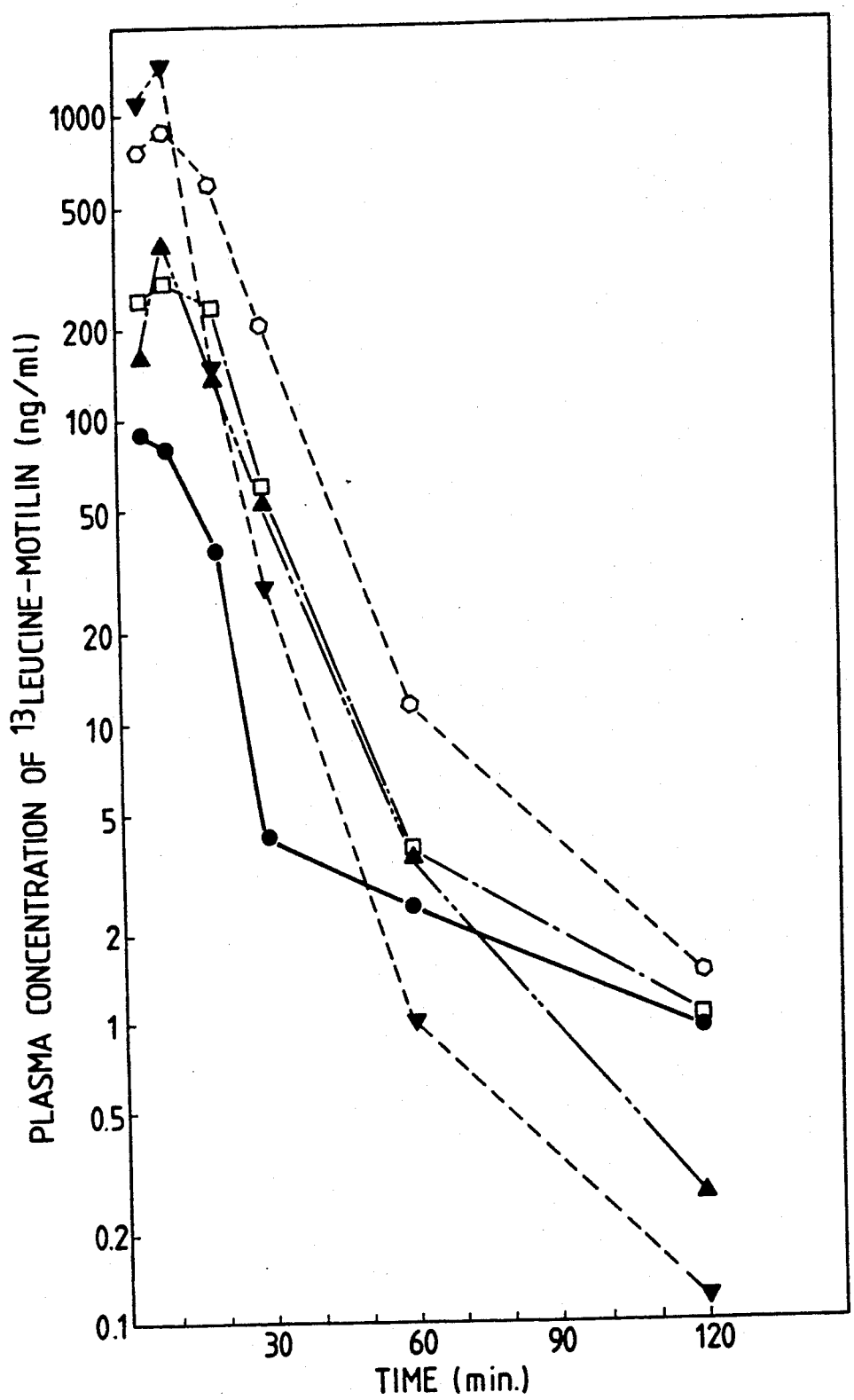
FIG. 2 shows the change in plasma concentration of $^{13}$leucine-motilin as the result of Test Example 3, wherein -○- shows the suppository of Example 3, -▲- shows that of Example 4, -□- shows that of Example 5, -▼- shows that of Example 6 and -●- shows that of Example 14.

FIG. 2 shows the results, while Table 3 shows Tmax, Cmax, AUC and biological availability.

The biological availability (BA) was calculated according to the following equation wherein the $AUC_0^\infty$ at the intravenous administration was referred to 66200 ng·min/ml.

$$BA = \frac{AUC_0^\infty \text{ at rectal administration}}{AUC_0^\infty \text{ at intravenous administration}}$$

TABLE 3

| Suppository | Tmax (min) | Cmax (ng/ml) | $AUC_0^\infty$ (ng · min/ml) | BA |
|---|---|---|---|---|
| Ex. 3 | 10 | 891 | 21,200 | 32.0 |
| Ex. 4 | 10 | 373 | 6,300 | 9.5 |
| Ex. 5 | 10 | 286 | 7,210 | 10.9 |
| Ex. 6 | 10 | 1,461 | 18,600 | 28.1 |
| Ex. 14 | 5 | 89 | 1,660 | 2.5 |

TEST EXAMPLE 4

The motilin suppositories prepared in Examples 7 to 10 and Reference Example 4 were rectally administered to beagles weighing approximately 12 kg, which had fasted for 24 hours, each in a dose of 1.0 mg/kg. The blood of each animal was collected from its forefoot vein 5, 10, 20, 30, 60 and 90 minutes after the administration. Then the plasma was separated and the motilin concentration was determined by RIA.

Figure 3:
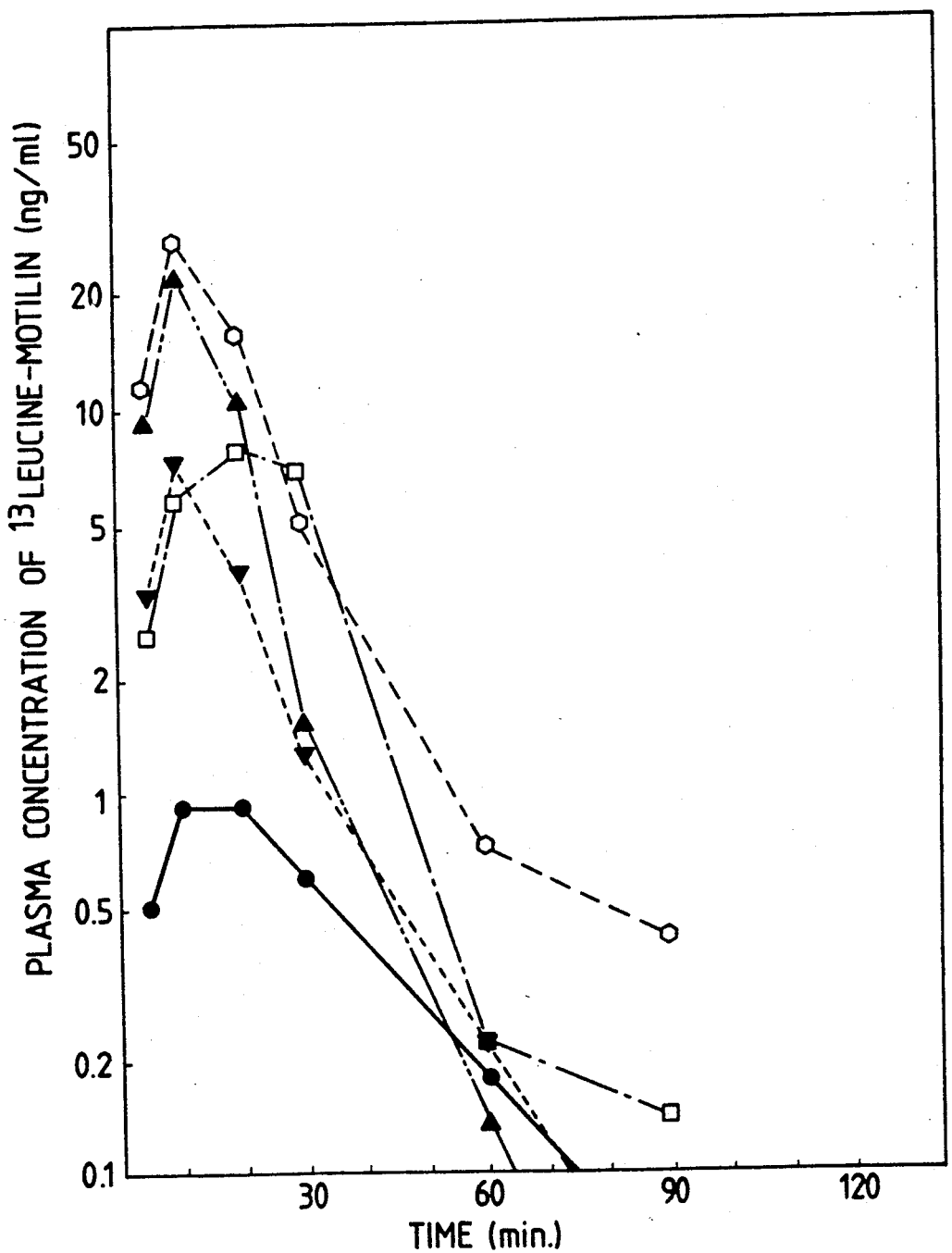
FIG. 3 shows the change in plasma concentration of $^{13}$leucine-motilin as the result of Test Example 4, wherein -○- shows the suppository of Example 7, -▲- shows that of Example 8, -□- shows that of Example 9, -▼- shows that of Example 10 and -●- shows that of Example 15.

FIG. 3 shows the results, while Table 4 shows Tmax, Cmax, $AUC_0^\infty$ and BA.

The biological availability (BA) was calculated by referring the $AUC_0^\infty$ at the intravenous administration to as 27,647 ng·min/ml.

TABLE 4

| Suppository | Tmax (min) | Cmax (ng/ml) | $AUC_0^\infty$ (ng · min/ml) | BA |
|---|---|---|---|---|
| Ex. 7 | 10 | 27.0 | 561 | 2.03 |
| Ex. 8 | 10 | 22.3 | 354 | 1.28 |
| Ex. 9 | 20 | 7.8 | 283 | 1.02 |

TABLE 4-continued

| Suppository | Tmax (min) | Cmax (ng/ml) | $AUC_0^\infty$ (ng · min/ml) | BA |
|---|---|---|---|---|
| Ex. 10 | 10 | 7.1 | 137 | 0.50 |
| Ex. 15 | 10 | 0.9 | 38 | 0.12 |

TEST EXAMPLE 5

The motilin suppositories prepared in Examples 11 to 13 and Reference Example 5 were rectally administered to rabbits each weighing approximately 2.5 kg (each group had six animals), which had fasted for 16 hours, each in a dose of 1.0 mg/kg.

The blood of each animal was collected from its oticus vein 5, 10, 20, 30, 60, 120 and 240 minutes after the administration. Then the plasma was separated and the motilin concentration was determined by RIA.

Figure 4:
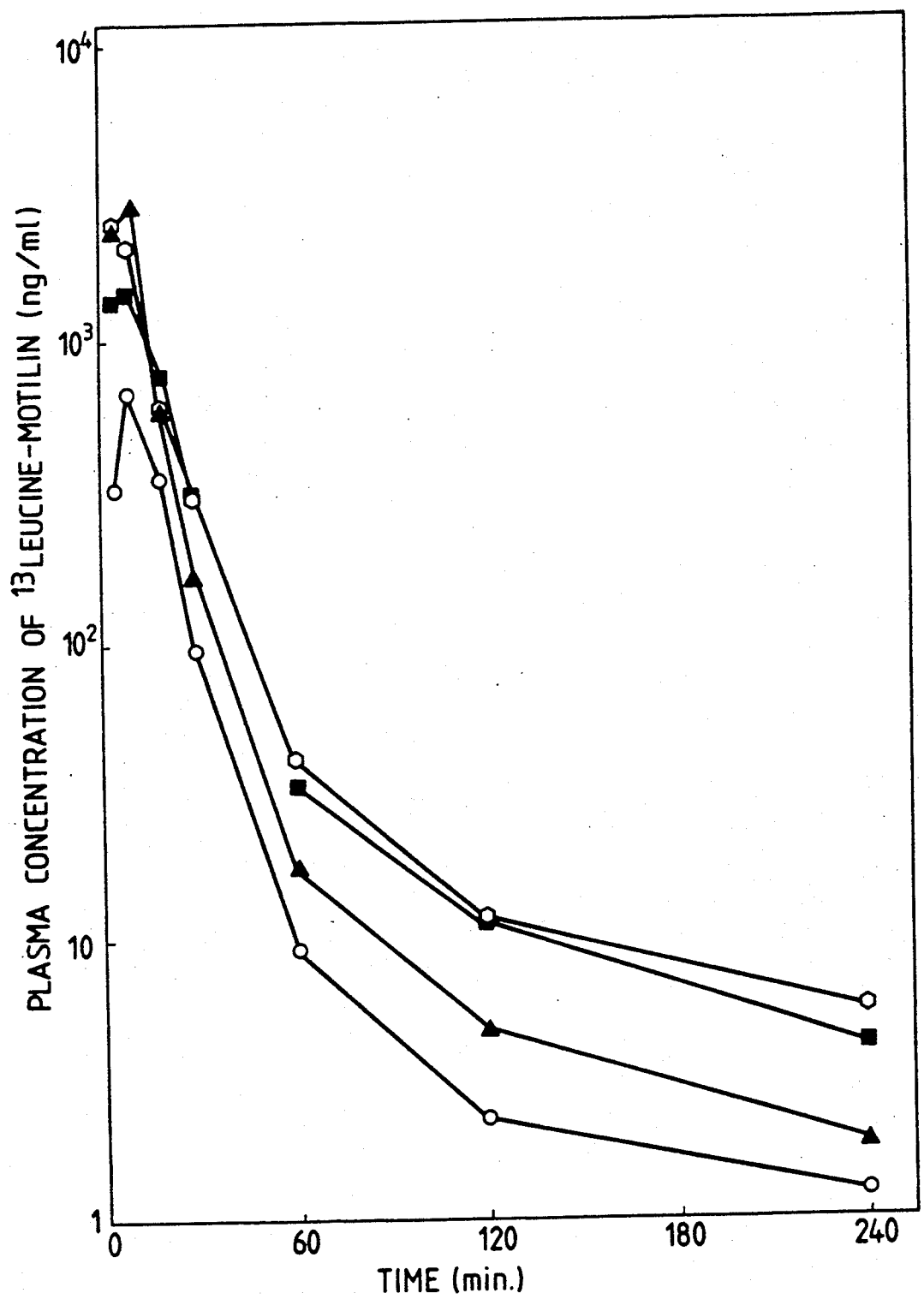
FIG. 4 shows the change in plasma concentration of $^{13}$methiOnine motilin as the result Of Test Example 5, wherein -■- shows the suppository of Example 11, -○- shows that of Example 12, -▲- shows that of Example 13 and -○- shows that of Example 16.

FIG. 4 shows the results, while Table 5 shows Tmax, Cmax, $AUC_0^\infty$ and BA.

The biological availability (BA) was calculated by referring the $AUC_0^\infty$ at the intravenous administration to as 68,872 ng·min/ml.

TABLE 5

| Suppository | Tmax (min) | Cmax (ng/ml) | $AUC_0^\infty$ (ng · min/ml) | BA |
|---|---|---|---|---|
| Ex. 11 | 10 | 1,403 | 33,321 | 48.4 |
| Ex. 12 | 5 | 2,455 | 42,256 | 61.4 |
| Ex. 13 | 10 | 2,849 | 43,859 | 63.7 |
| Ex. 16 | 10 | 661 | 12,582 | 18.3 |

Thus the motilin preparation of the present invention is useful as a rectal suppository which provides an effective delivery vehicle for the physiologically active peptide maintaining bioavailability.

While the invention has been described in detail and with reference to specific embodiments thereof, it will be apparent to one skilled in the art that various changes and modifications can be made therein without departing from the spirit and scope thereof.

WHAT IS CLAIMED IS:

1. A pharmaceutical composition for rectal administration comprising a therapeutically effective quantity of motilin together with a pH controller capable of adjusting the pH value of the patient's intrarectal fluid to 8.0 to 10.0.

2. The pharmaceutical composition of claim 1, further containing a membrane-permeation promoter and/or a protease inhibitor.

3. The pharmaceutical composition of claim 1, containing from about 0.05 to about 5% by weight motilin.

4. The pharmaceutical composition of claim 1, or containing from about 0.1 to about 2% by weight motilin.

5. The pharmaceutical composition of claim 1 in which the pH controller adjusts the patient's intrarectal fluid to a pH of 8.5 to 9.5.

6. The pharmaceutical composition of claim 1 in which the pH controller is hydrochloric acid/sodium barbital, hydrochloric acid/trisaminomethane, hydrochloric acid/sodium borate, hydrochloric acid/aminomethylpropanediol, hydrochloric acid/sodium dimethylglycinate, sodium carbonate/sodium bicarbonate, sodium carbonate/sodium borate, monobasic potassium phosphate/sodium boreate, ammonium chloride/ammonia, glycine/sodium hydroxide or glycine/arginine.

7. The pharmaceutical composition of claim 2 in which the membrane-permeation promoter is a fatty acid having 6 to 18 carbon atoms, a salt of a fatty acid having 6 to 18 carbon atoms, a bile acid, or a salt of a bile acid.

8. The pharmaceutical composition of claim 2 in which the membrane-permeation promoter is a straight-chain saturated fatty acid having 8 to 12 carbon atoms or a salt thereof.

9. The pharmaceutical composition of claim 2 in which the protease inhibitor is a peptide protease inhibitor.

10. The pharmaceutical composition of claim 2 in which the protease inhibitor is a compound having a sulfhydryl group.

11. A rectal suppository comprising from about 0.05 to 5% by weight motilin together with a pH controller capable of adjusting the pH value of the patient's intrarectal fluid to 8.0 to 10.0.

12. The rectal suppository of claim 11, containing from about 0.1 to about 2% by weight motilin.

13. The rectal suppository of claim 11, in which the pH controller adjusts the pH of the patient's intrarectal fluid to pH 8.5 to 9.5.

14. The rectal suppository of claim 11, keep further containing a membrane-permeation promoter and/or a protease inhibitor.

15. A method of administering motilin to a patient in need of same comprising inserting a rectal suppository comprising from about 0.05 to 5% by weight motilin together with a pH controller capable of adjusting the pH value of the patient's intrarectal fluid to a pH of 8.0 to 10.0.

16. A method of stimulating gastric motor activity in a patient in need of same comprising inserting a rectal suppository comprising from about 0.05 to 5% by weight motilin together with a pH controller capable of adjusting the pH value of the patient's intrarectal fluid to a pH of 8.0 to 10.0.

* * * * *